(12) United States Patent
Eddy

(10) Patent No.: US 9,675,735 B2
(45) Date of Patent: *Jun. 13, 2017

(54) CATHETERS HAVING AN ANTIMICROBIAL TREATMENT

(71) Applicant: Parasol Medical LLC, Buffalo Grove, IL (US)

(72) Inventor: Patrick E. Eddy, Allendale, MI (US)

(73) Assignee: Parasol Medical LLC, Buffalo Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/831,243

(22) Filed: Aug. 20, 2015

(65) Prior Publication Data

US 2015/0352320 A1 Dec. 10, 2015

Related U.S. Application Data

(63) Continuation-in-part of application No. 14/216,020, filed on Mar. 17, 2014.
(Continued)

(51) Int. Cl.
*A61L 29/08* (2006.01)
*A61L 29/16* (2006.01)
(Continued)

(52) U.S. Cl.
CPC ............... *A61L 29/08* (2013.01); *A61L 29/06* (2013.01); *A61L 29/16* (2013.01); *A61M 1/285* (2013.01);
(Continued)

(58) Field of Classification Search
CPC ............... A61L 29/06; A61L 2300/208; A61L 2300/404; A61L 29/16; A61L 2300/606;
(Continued)

(56) References Cited

U.S. PATENT DOCUMENTS 4,603,152 A * 7/1986 Laurin ................... A01N 25/10
106/15.05
5,079,004 A 1/1992 Blank et al.
(Continued)

FOREIGN PATENT DOCUMENTS

WO 2008097599 A2 8/2008
WO WO 2008/097599 A2 * 8/2008 ............... A61B 5/03

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

*Primary Examiner* — Aradhana Sasan
(74) *Attorney, Agent, or Firm* — Price Heneveld LLP

(57) ABSTRACT

A vascular access product is provided having a component with a plurality of external surfaces. At least one of the surfaces is coated with an antimicrobial treatment, wherein the antimicrobial material comprises a silane quaternary ammonium salt. The silane quaternary ammonium salt may comprise 3-(trimethoxysilyl) propyldimethyloctadecyl ammonium chloride. The vascular access product may be IV administration tubing, a catheter and the associated caps, luers, Y sites, connectors, drip chambers, PICC lines, stopcocks and similar IV components such as needleless IV connectors having valve mechanisms.

6 Claims, 7 Drawing Sheets

Related U.S. Application Data

(60) Provisional application No. 62/039,539, filed on Aug. 20, 2014, provisional application No. 61/786,930, filed on Mar. 15, 2013.

(51) Int. Cl.

| | |
|---|---|
| *A61L 29/06* | (2006.01) |
| *A61M 39/26* | (2006.01) |
| *A61M 1/28* | (2006.01) |
| *A61M 1/36* | (2006.01) |
| *A61M 5/14* | (2006.01) |
| *A61M 25/00* | (2006.01) |

(52) U.S. Cl.
CPC .......... *A61M 1/3661* (2014.02); *A61M 39/26* (2013.01); *A61L 2300/208* (2013.01); *A61L 2300/404* (2013.01); *A61L 2300/606* (2013.01); *A61M 5/14* (2013.01); *A61M 2025/006* (2013.01); *A61M 2039/267* (2013.01); *A61M 2202/0021* (2013.01); *A61M 2202/0413* (2013.01); *A61M 2205/0205* (2013.01); *A61M 2210/12* (2013.01)

(58) Field of Classification Search
CPC .. A61L 29/08; C08L 83/04; A61M 2039/267; A61M 39/26; A61M 1/285; A61M 1/3661; A61M 2202/0021; A61M 5/14; A61M 2025/006; A61M 2202/00
See application file for complete search history.

(56) References Cited

U.S. PATENT DOCUMENTS

| | | | |
|---|---|---|---|
| 5,411,585 A * | 5/1995 | Avery | A01N 55/00 |
| | | | 106/287.1 |
| 5,428,078 A | 6/1995 | Cohen et al. | |
| 5,685,866 A | 11/1997 | Lopez | |
| 5,959,014 A | 9/1999 | Liebeskind et al. | |
| 6,224,579 B1 | 5/2001 | Modak et al. | |
| 6,821,943 B2 | 11/2004 | Avery et al. | |
| 7,045,673 B1 | 5/2006 | Batich et al. | |
| 7,709,694 B2 | 5/2010 | Batich et al. | |
| 7,790,217 B2 | 9/2010 | Toreki et al. | |
| 8,025,120 B2 | 9/2011 | Eddy | |
| 8,491,922 B2 | 7/2013 | Eddy | |
| 2006/0223962 A1 * | 10/2006 | Getman | A01N 25/34 |
| | | | 528/10 |
| 2007/0042198 A1 | 2/2007 | Schonemyr et al. | |
| 2007/0218096 A1 | 9/2007 | Wooley | |
| 2008/0193497 A1 * | 8/2008 | Samuelsen | A01N 37/12 |
| | | | 424/405 |
| 2008/0260804 A1 | 10/2008 | Morris et al. | |
| 2011/0282302 A1 | 11/2011 | Lopez et al. | |
| 2012/0157567 A1 * | 6/2012 | Ou | C08L 83/04 |
| | | | 523/122 |
| 2012/0173274 A1 | 7/2012 | Rensvold et al. | |
| 2014/0276456 A1 * | 9/2014 | Eddy | A61L 29/06 |
| | | | 604/249 |
| 2015/0352320 A1 | 12/2015 | Eddy | |

* cited by examiner

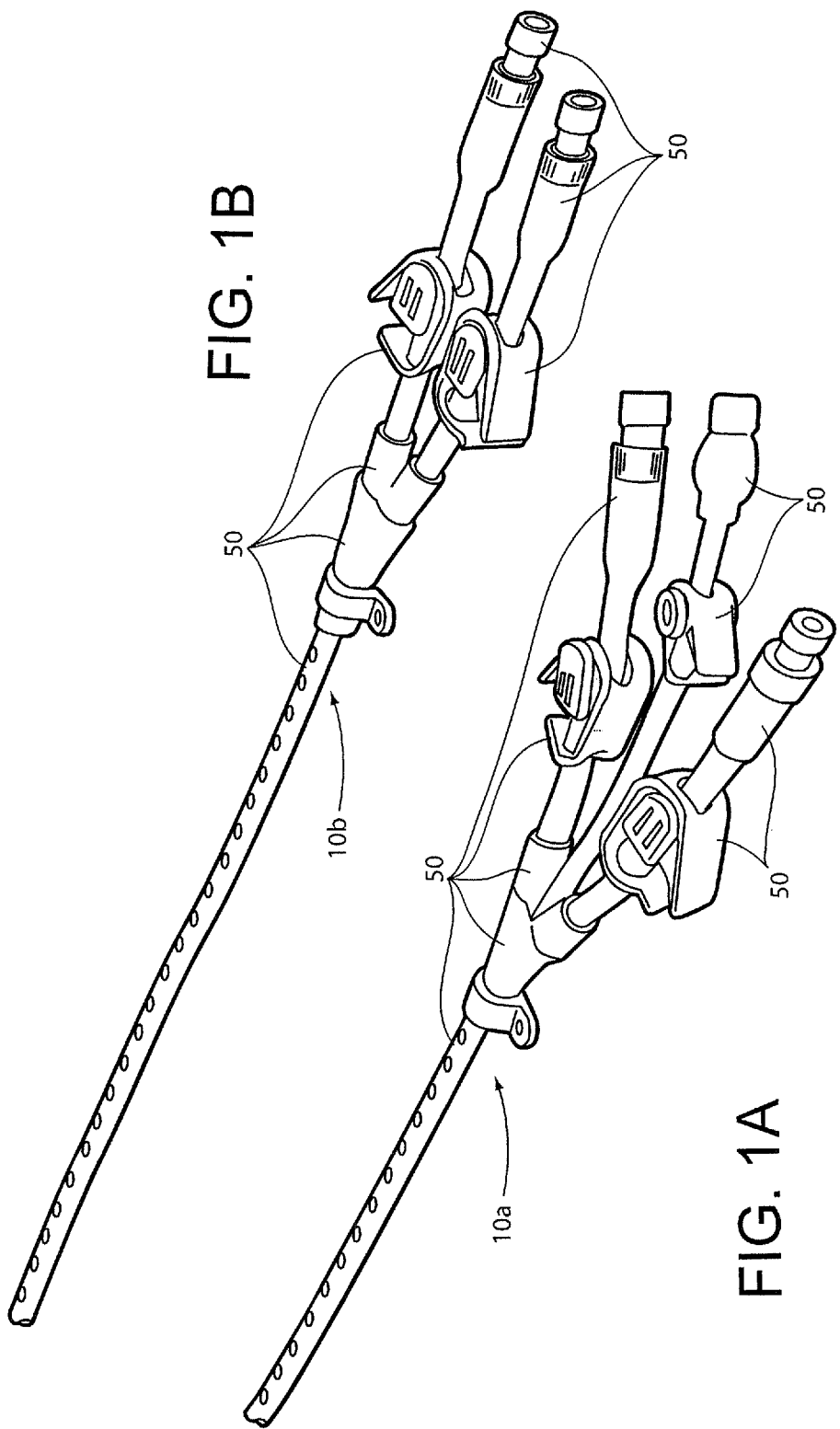

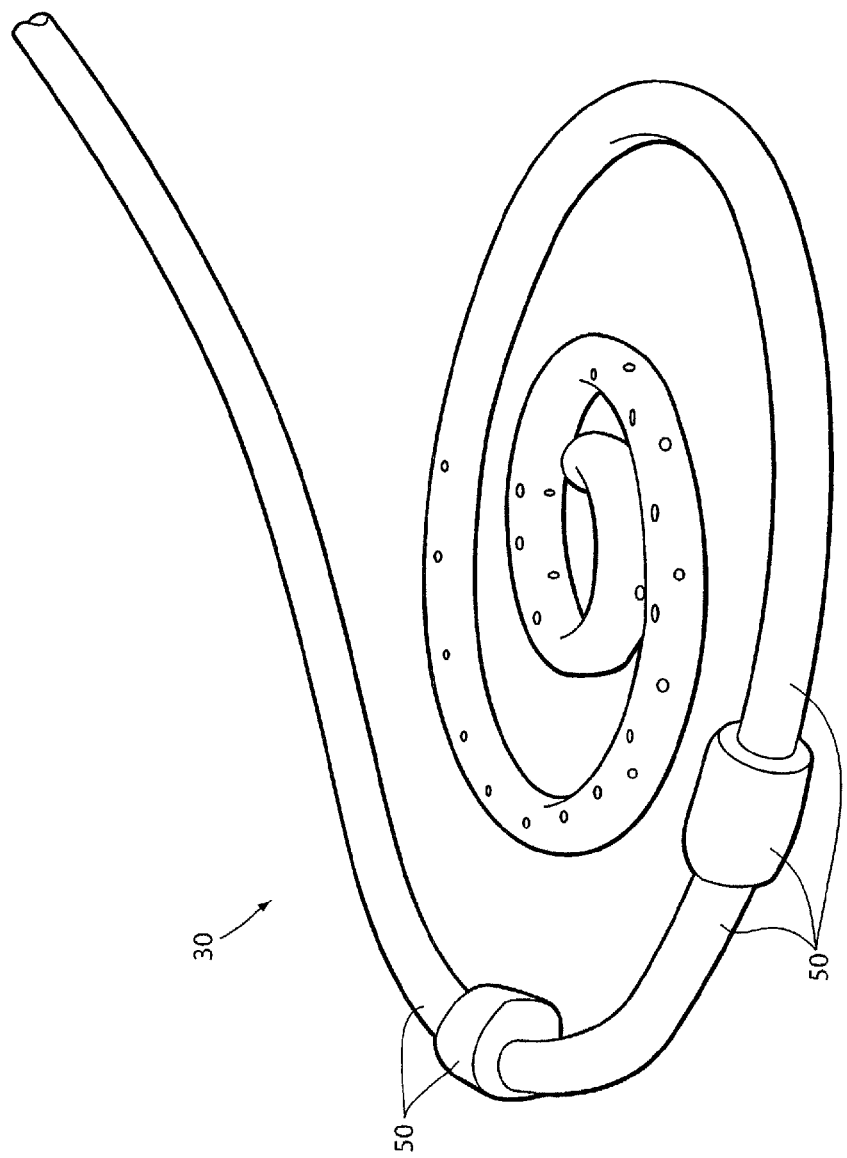

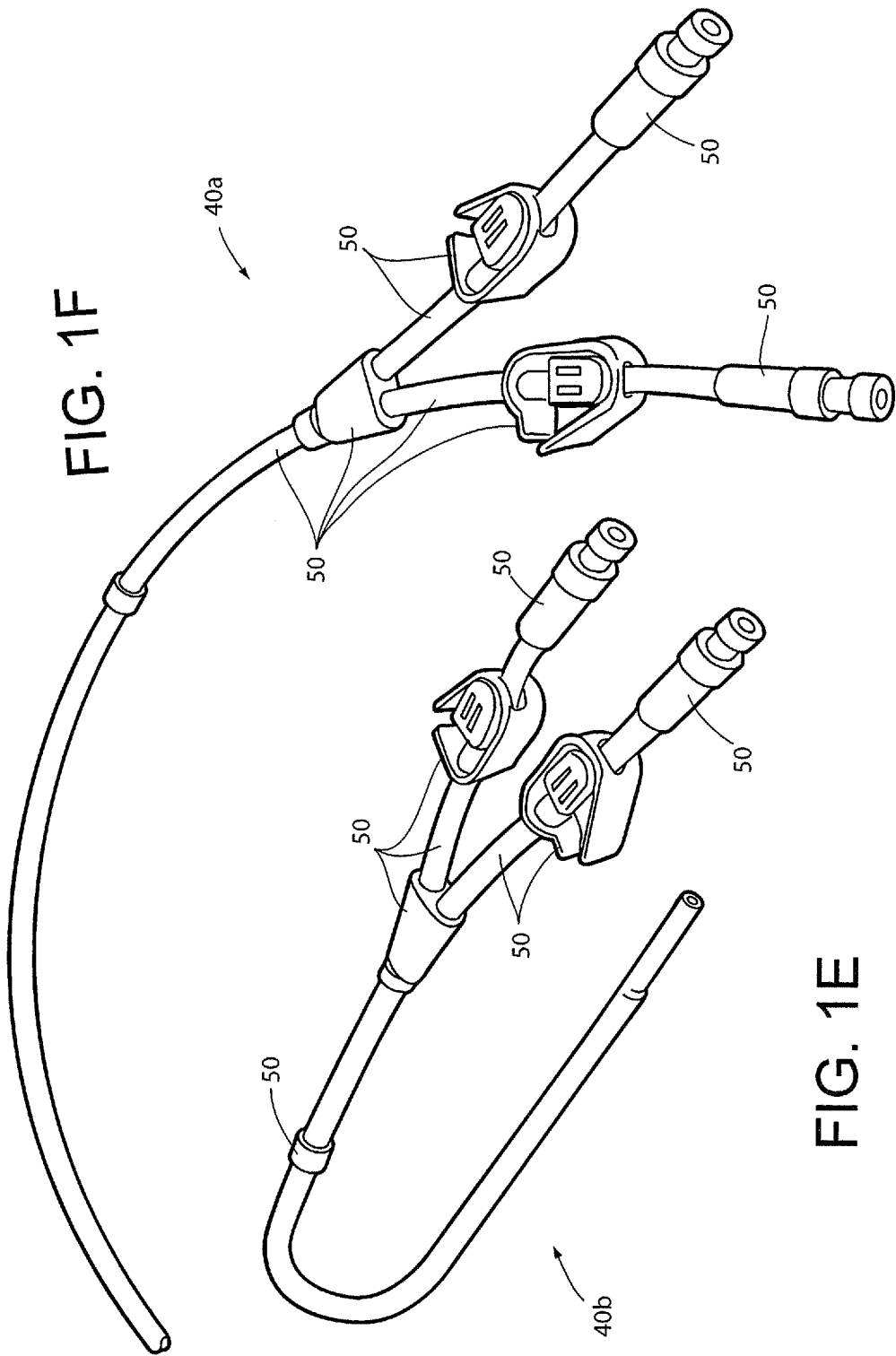

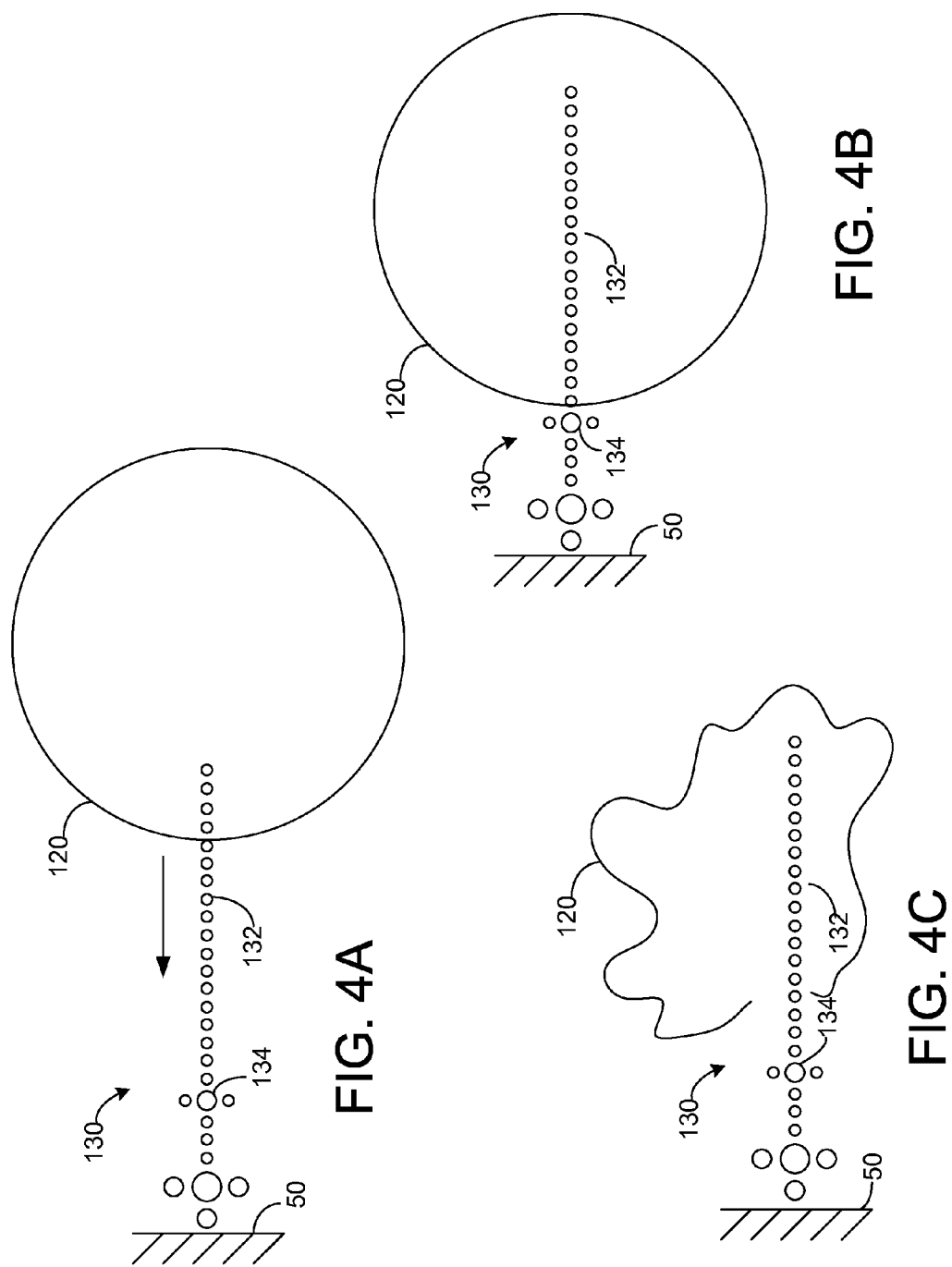

CATHETERS HAVING AN ANTIMICROBIAL TREATMENT

CROSS-REFERENCE TO RELATED APPLICATIONS

This application claims priority under 35 U.S.C. §119(e) upon U.S. Provisional Patent Application No. 62/039,539, entitled "CATHETERS HAVING AN ANTIMICROBIAL TREATMENT" filed on Aug. 20, 2014, by Patrick E. Eddy. This application is a continuation-in-part of U.S. patent application Ser. No. 14/216,020, entitled "INTRAVENOUS CONNECTOR HAVING ANTIMICROBIAL TREATMENT" filed on Mar. 17, 2014, by Patrick E. Eddy, now U.S. Pat. No. 9,433,708, which claims priority to U.S. Provisional Patent Application No. 61/786,930, entitled "INTRAVENOUS CONNECTOR HAVING ANTIMICROBIAL TREATMENT" filed on Mar. 15, 2013, by Patrick E. Eddy. The entire disclosures of each of the above applications are incorporated herein by reference.

BACKGROUND OF THE INVENTION

The present invention generally relates to vascular access products such as intravenous (IV) administration tubing, catheters and the associated caps, luers, Y sites, connectors, drip chambers, peripherally inserted central catheter (PICC) lines, stopcocks and similar IV components.

Vascular access products such as IV administration tubing, catheters and the associated caps, luers, Y sites, connectors, drip chambers, PICC lines, stopcocks and similar IV components such as needleless IV connectors having valve mechanisms are known in the art. Examples of such vascular access products are available from Health Line Medical Products of Centerville, Utah, and are visible on their website at www.hlic.net.

An example of a valve mechanism for a needleless IV connector is the medical valve described in U.S. Pat. No. 5,685,866 assigned to ICU Medical, Inc. who also makes such needleless IV connectors under the trademark MicroClave®. One of the MicroClave® needleless IV connectors is available with an antimicrobial treatment, where the antimicrobial treatment consists of ionic silver. Such ionic silver, however, is subject to leaching over time.

SUMMARY OF THE INVENTION

According to an embodiment of the present invention, a vascular access product is provided comprising a component having a plurality of external surfaces, wherein at least one of said surfaces is coated with an antimicrobial treatment, wherein said antimicrobial material comprises a silane quaternary ammonium salt.

According to another embodiment of the present invention, a catheter is provided comprising a component having a plurality of external surfaces, wherein at least one of said surfaces is coated with an antimicrobial treatment, wherein said antimicrobial material comprises a silane quaternary ammonium salt.

In one or more of these embodiments, the silane quaternary ammonium salt may comprise 3-(trimethoxysilyl) propyldimethyloctadecyl ammonium chloride.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIGS. 1A and 1B show acute hemo-dialysis catheters according to one embodiment;

FIG. 1D shows a peritoneal dialysis catheter according to another embodiment;

FIGS. 1E and 1F show chronic hemo-dialysis catheters according to another embodiment;

FIG. 4A is a schematic representation of the monomer shown in FIGS. 2 and 3 illustrating a first step in the manner by which the monomer destroys a microbe;

FIG. 4B is a schematic representation of the monomer shown in FIGS. 2 and 3 illustrating a second step in the manner by which the monomer destroys a microbe; and FIG. 4C is a schematic representation of the monomer shown in FIGS. 2 and 3 illustrating a third step in the manner by which the monomer destroys a microbe.

DETAILED DESCRIPTION OF THE EMBODIMENTS

Figure 1C:
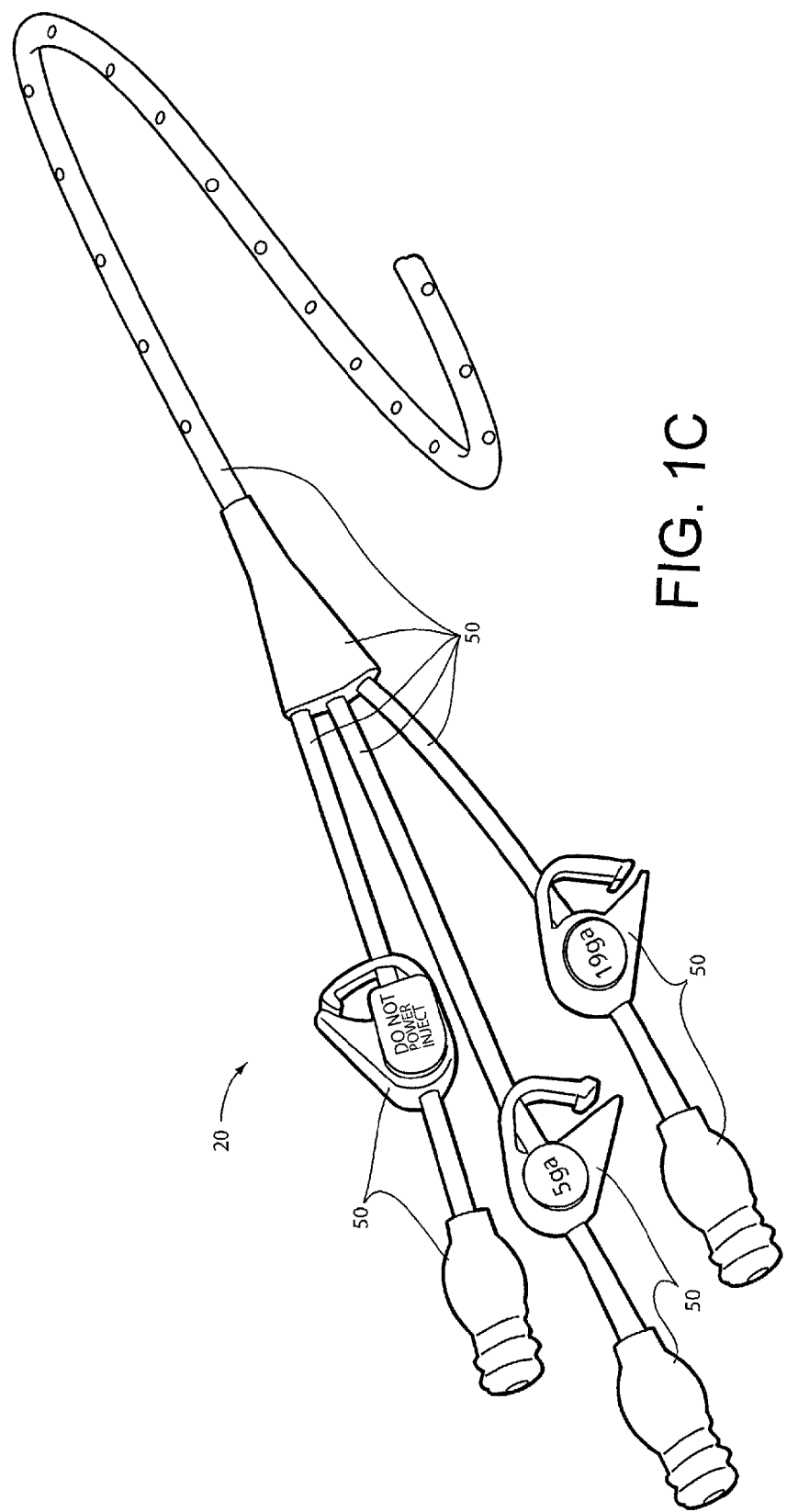
FIG. 1C shows a PICC line according to another embodiment.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

As noted above, the embodiments described herein pertain to vascular access products such as catheters. Because such vascular access products may provide a path into the patient's bloodstream, it is important that they do not harbor bacteria or other microbes.

Novel vascular access products are disclosed herein that not only provide the requisite properties for such vascular access products, but also eliminate bacteria on contact. As discussed below, the components of the vascular access products are either treated with or formed with an antimicrobial substance comprising a silane quaternary ammonium salt. Examples of vascular access products that may be so treated are shown in FIGS. 1A-1D.

FIGS. 1A and 1B show an example of a first embodiment wherein acute hemo-dialysis catheters 10a and 10b have one or more of their external surfaces 50 coated with an antimicrobial treatment.

FIG. 1C shows an example of a second embodiment wherein a PICC line 20 has one or more of its external surfaces 50 coated with an antimicrobial treatment.

FIG. 1D shows an example of a third embodiment wherein a peritoneal dialysis catheter 30 has one or more of its external surfaces 50 coated with an antimicrobial treatment.

FIGS. 1E and 1F show an example of a fourth embodiment wherein chronic hemo-dialysis catheters 40a and 40b have one or more of their external surfaces 50 coated with an antimicrobial treatment.

In general, the antimicrobial treatment may be applied to all surfaces 50 of the above vascular access products (10a,

10b, 20, 30, 40a, 40b). However, it is possible to obtain benefits by treating at least one of the surfaces treated with the antimicrobial treatment, and particularly the surfaces contacting the patient.

The surfaces 50 of the vascular access products are coated with an antimicrobial treatment that may be sprayed onto the surfaces using a solution and/or may be applied using wipes soaked in such a solution. Suitable wipes and solutions are disclosed in commonly assigned U.S. Pat. No. 8,491,922, the entire disclosure of which is incorporated herein by reference. In this case, the antimicrobial material is again one of the silane quaternary ammonium salts described above.

In a preferred form, the antimicrobial treatment solution contains 30-50 percent by volume isopropyl alcohol and 50-70 percent by volume antimicrobial treatment substance, which is preferably a silane quaternary ammonium salt having an unreacted organofunctional silane. If the antimicrobial treatment solution is applied by spraying or dipping, the solution most preferably includes 50 percent by volume isopropyl alcohol and 50 percent by volume of the unreacted antimicrobial treatment substance. If the solution is applied using the wipes, the solution is preferably 30 percent by volume isopropyl alcohol and 70 percent by volume of the unreacted antimicrobial treatment substance.

The isopropyl alcohol may have a concentration of 70-90 percent by volume. By providing the unreacted organofunctional silane in isopropyl alcohol, the organofunctional silane does not react with the wipe substrates or the inside of the wipe container such that it is free to later react and permanently covalently bond with the inner and outer surfaces 50 of the vascular access products. Isopropyl alcohol is preferred as it evaporates quickly once the solution is wiped onto the treated surface to allow the unreacted organofunctional silane to more quickly react with the treated surface.

The preferred organofunctional silane quaternary ammonium salt also prevents odor, staining and product deterioration that may be associated with microbe contamination. The preferred organofunctional silane quaternary ammonium salt is also beneficial because it permanently bonds to a treated surface, covers a broad spectrum of activity with no negative effects or drawbacks, and is easily incorporated and easily verifiable.

The preferred organofunctional silane quaternary ammonium salt is designed to react and create a covalent bond with the surfaces of the plastic components. The reacted substance is held onto those surfaces until the covalent bond is broken. Tests have shown that most industrial cleaners or disinfectants will not remove the preferred antimicrobial treatment substance. The method of removal is by abrasion.

The preferred silane quaternary ammonium salt includes an active ingredient of 3-(trimethoxysilyl) propyldimethyloctadecyl ammonium chloride and other inert ingredients. The silane quaternary ammonium salt preferably includes about 0.1 to 50 percent by weight of the 3-(trimethoxysilyl) propyldimethyloctadecyl ammonium chloride and most preferably includes about 5 percent by weight of the 3-(trimethoxysilyl) propyldimethyloctadecyl ammonium chloride. Such silane quaternary ammonium salts are available from Aegis Environments of Midland, Mich., which is identified as "AEM 5772-5 Antimicrobial," and from Piedmont Chemical Industries I, LLC of High Point, N.C., which is identified as "PROMOFRESH X 105." The antimicrobial treatment solution with the isopropyl alcohol is available from MicrobeCare, LLC of Allendale, Mich., under the trademark MICROBECARE™.

The above described silane quaternary ammonium salt is preferred because it is an organofunctional silane antimicrobial treatment substance that is substantially free from arsenic, silver, tin, heavy metals and polychlorinated phenols; copper; or a silver-ion emitter. In addition, it not only eliminates bacteria on contact, but it remains on the treated surfaces 50 and kills any bacteria subsequently contacting these surfaces. Such treatment preferably lasts at least one week, more preferably several months, and most preferably indefinitely.

Figure 2:
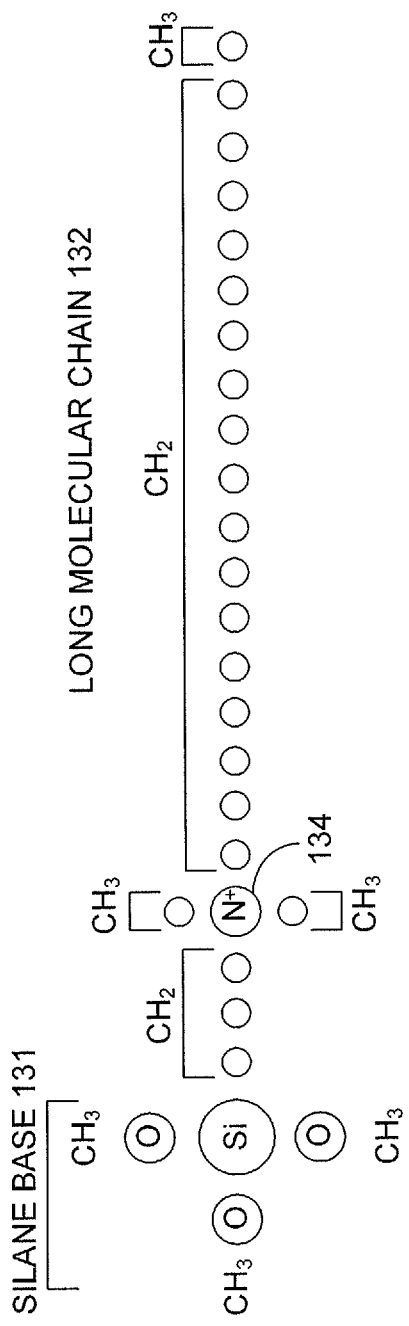
FIG. 2 is a schematic representation of a monomer that may be used in the embodiments described herein as an antimicrobial treatment substance.
Figure 3:
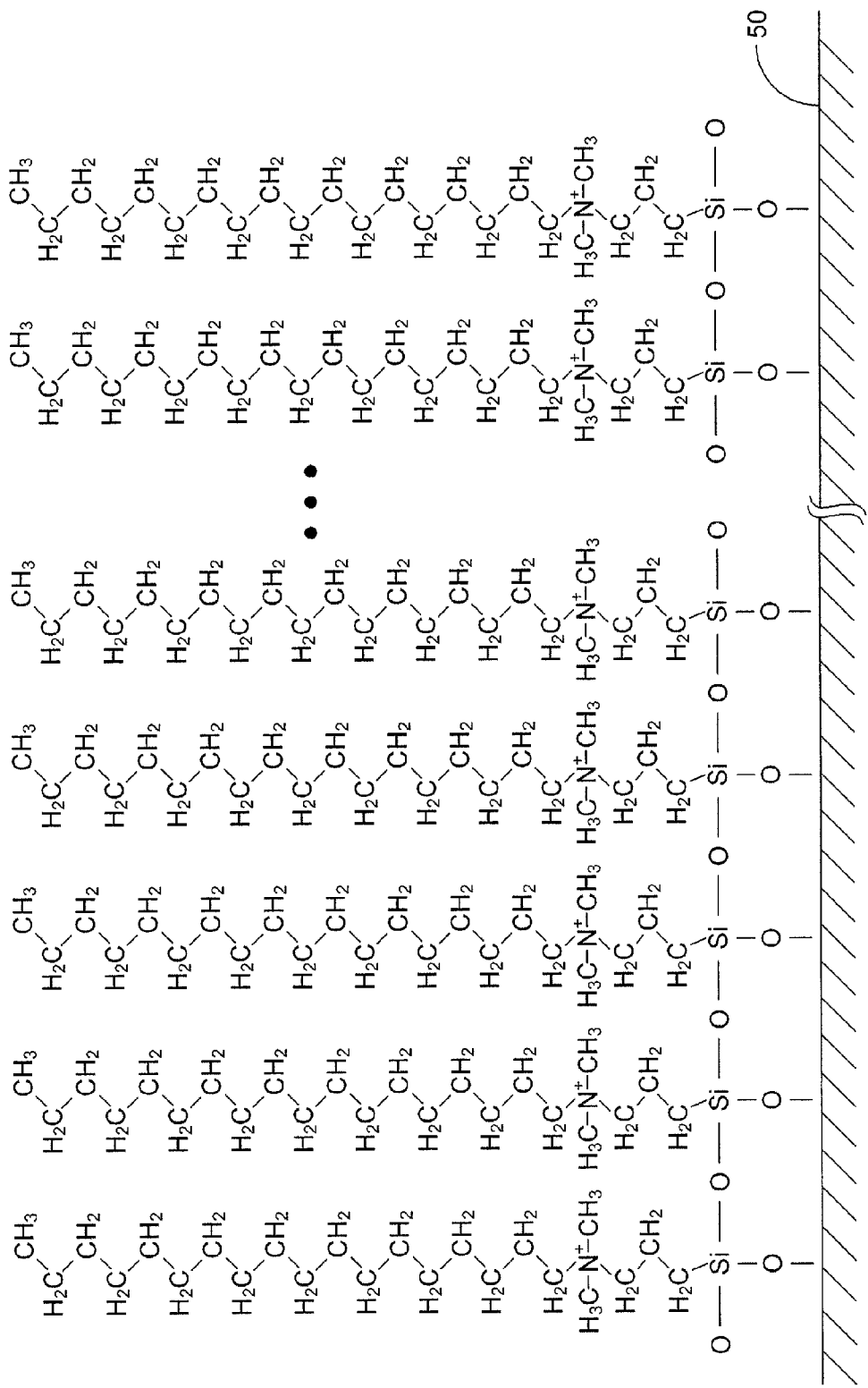
FIG. 3 is a schematic representation of a plurality of the monomers shown in FIG. 2 as applied to a treated surface.

FIG. 2 shows a schematic representation of a monomer form 130 of a preferred organofunctional silane serving as the antimicrobial treatment substance. As illustrated, monomer 130 includes a silane base 131 for bonding to a surface 50, a positively charged nitrogen molecule 134, and a long molecular chain 132. As shown in FIG. 3, the silane bases of these monomers covalently and permanently bond to each other and to the surface 50 to be treated in such a way that the long molecular chains are aligned and pointing outward from the surface 50. This tight bonding provides a micropolymer network that serves as a protective coating on the outside of the surface 50 that destroys any microbes that come into contact.

The manner by which the preferred organofunctional silane destroys microbes is illustrated in FIGS. 4A-4C. Such microbes may include bacteria, mold, mildew, algae, etc. As shown in FIG. 4A, the cell membrane 120 of the microbe is attracted to the treated surface 50 of the vascular access product and then is punctured by the long molecular chain 132 of the monomer 130. As the microbe is drawn closer because of the positive-negative ion exchange, the monomer 130 penetrates further into the cell membrane 120 as shown in FIG. 4B. Once the cell membrane 120 is penetrated deeply, it is physically ruptured by a sword-like action and then electrocuted by a positively charged nitrogen molecule 134 of the monomer 130, thus destroying the microbe as illustrated in FIG. 4C. Thus, the microbes are eliminated without "using up" any of the antimicrobial active ingredients, which remain on the surfaces 50 ready to continue protecting the treated item against further microbial contamination.

The preferred organofunctional silane is designed to react and create a covalent bond with the surfaces 50 of the vascular access product. The reacted substance is held onto those surfaces 50 until the covalent bond is broken. Tests have shown that most industrial cleaners or disinfectants will not remove the preferred antimicrobial treatment substance. The method of removal is by abrasion. In the event that the vascular access product or at least a part of the vascular access product is made of silicone, the antimicrobial material may be integrally formed within the silicone. In general, silicones are formed of slurries processed at relatively low temperatures. These low temperatures allow the antimicrobial material to be mixed in with the slurry and therefore integrated within the resulting foam or silicone part. The percentage of antimicrobial material in the slurry may vary from 0.001% to 20% by weight.

Although the invention is described with respect to particular constructions of the vascular access products shown in FIGS. 1A-1D, the constructions thereof may vary. Also, the present invention may be applied to arterial connectors and IV connectors.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

What is claimed is:

1. A vascular access product comprising:
a component having a plurality of external surfaces, wherein at least one of said surfaces is coated with an antimicrobial treatment,
wherein said antimicrobial treatment comprises a silane quaternary ammonium salt,
wherein said antimicrobial treatment comprises an antimicrobial treatment solution comprising said silane quaternary ammonium salt and isopropyl alcohol,
wherein the antimicrobial treatment solution comprises about 30 percent to about 50 percent by volume of isopropyl alcohol,
wherein the antimicrobial treatment solution comprises about 50 percent to about 70 percent by volume of said silane quaternary ammonium salt,
wherein said silane quaternary ammonium salt includes an unreacted organofunctional silane to promote bonding to the surfaces of the component, and
wherein said silane quaternary ammonium salt comprises 0.1 to 5 percent by weight 3-(trimethoxysilyl) propyldimethyloctadecyl ammonium chloride.

2. The vascular access product of claim 1, wherein said antimicrobial treatment is substantially free from arsenic, silver, tin, heavy metals and polychlorinated phenols.

3. The vascular access product of claim 1, wherein the antimicrobial treatment is covalently bonded to the at least one of said surfaces and is capable of emitting ions that aid in the destruction of a microbe.

4. The vascular access product of claim 1, wherein said vascular access product is selected from the group consisting of a catheter and a PICC line.

5. A catheter comprising:
a component having a plurality of external surfaces, wherein at least one of said surfaces is coated with an antimicrobial treatment,
wherein said antimicrobial treatment comprises a silane quaternary ammonium salt,
wherein said antimicrobial treatment comprises an antimicrobial treatment solution comprising said silane quaternary ammonium salt and isopropyl alcohol,
wherein the antimicrobial treatment solution comprises about 30 percent to about 50 percent by volume of isopropyl alcohol,
wherein the antimicrobial treatment solution comprises about 50 percent to about 70 percent by volume of said silane quaternary ammonium salt,
wherein said silane quaternary ammonium salt includes an unreacted organofunctional silane to promote bonding to the surfaces of the component, and
wherein said silane quaternary ammonium salt comprises 0.1 to 5 percent by weight 3-(trimethoxysilyl) propyldimethyloctadecyl ammonium chloride.

6. The catheter of claim 5, wherein said catheter is selected from the group consisting of an acute hemo-dialysis catheter; a chronic hemo-dialysis catheter; and a peritoneal dialysis catheter.

* * * * *